United States Patent [19]

Richtzenhain et al.

[11] 4,069,265
[45] Jan. 17, 1978

[54] STABILIZATION OF 1,1,1-TRICHLOROETHANE WITH A FOUR COMPONENT SYSTEM

[75] Inventors: Hermann Richtzenhain, Much-Schwellenbach; Rudolf Stephan, Troisdorf-Sieglar, both of Germany

[73] Assignee: Dynamit Nobel Aktiengesellschaft, Troisdorf, Germany

[21] Appl. No.: 662,999

[22] Filed: Mar. 1, 1976

Related U.S. Application Data

[60] Division of Ser. No. 408,955, Oct. 23, 1973, Pat. No. 3,959,397, which is a continuation-in-part of Ser. No. 60,173, June 29, 1970, Pat. No. 3,787,509, which is a division of Ser. No. 805,923, Jan. 5, 1969, Pat. No. 3,590,088, which is a division of Ser. No. 609,681, Jan. 16, 1967, Pat. No. 3,445,532, which is a continuation of Ser. No. 316,772, Oct. 16, 1963, abandoned.

[30] Foreign Application Priority Data

Oct. 18, 1962   Germany .................................. 40087

[51] Int. Cl.$^2$ ............................................. C07C 17/42
[52] U.S. Cl. ............................................. 260/652.5 R
[58] Field of Search ................................. 260/652.5 R

[56] References Cited

U.S. PATENT DOCUMENTS

| 3,049,571 | 8/1962 | Brown ........................ 260/652.5 R |
| 3,536,766 | 10/1970 | Mogford .................... 260/652.5 R |
| 3,959,397 | 5/1976 | Richtzenhain et al. ...... 260/652.5 R |

FOREIGN PATENT DOCUMENTS

| 592,942 | 2/1960 | Canada ......................... 260/652.5 R |
| 896,953 | 5/1962 | United Kingdom .......... 260/652.5 R |
| 1,236,921 | 7/1968 | United Kingdom .......... 260/652.5 R |

*Primary Examiner*—Delbert E. Gantz
*Assistant Examiner*—J. Thierstein
*Attorney, Agent, or Firm*—Burgess, Dinklage & Sprung

[57] ABSTRACT

A stabilized 1,1,1-trichloroethane composition containing, as stabilizer therefor, a mixture consisting of a nitrile, 1,4-dioxane, and nitromethane.

5 Claims, No Drawings

STABILIZATION OF 1,1,1-TRICHLOROETHANE WITH A FOUR COMPONENT SYSTEM

CROSS REFERENCE TO RELATED APPLICATIONS

This is a division, of application Ser. No. 408,955, filed Oct. 23, 1973 now U.S. Pat. No. 3,959,397 which is a continuation-in-part of application Ser. No. 60,173 of June 29, 1970, now U.S. Pat. No. 3,787,509, which, in turn, is a divisional application of Ser. No. 805,923 filed Jan. 5, 1969, now U.S. Pat. No. 3,590,088, which, in turn, is a divisional application of Ser. No. 609,681, filed Jan. 16, 1967, now U.S. Pat. No. 3,445,532 which, in turn, is a continuation of application Ser. No. 316,772, filed Oct. 16, 1963, now abandoned.

BACKGROUND OF THE INVENTION

1. Field of the Invention

This invention relates to a new and valuable 1,1,1-trichloroethane stabilized composition. More particularly, this invention relates to an improved 1,1,1-trichloroethane stabilized composition which contains, as stabilizer therefor, a three component stabilizer system. This invention is directed to improving the stability of 1,1,1-trichloroethane to reduce the marked tendency thereof to undergo decomposition.

DISCUSSION OF PRIOR ART

It is well known that halogen hydrocarbons such as vinyl chloride, vinylidene chloride, trichloroethane, trichloroethylene, perchloroethylene, and other aliphatic chlorinated hydrocarbons very easily undergo decomposition. This decomposition generally takes place at the simultaneous formation of acids and is caused, among other things, by the presence of light, air, or traces of water. It is further known that the splitting off of acids is greatly promoted by the presence of certain metals. Thus, for example, the decomposition reaction is catalyzed by iron, aluminum, magnesium and alloys of such metals.

The decomposition reaction can be so violent in the case of some of these compounds, that the further use and processing of these halogen hydrocarbons in metal vessels is possible only with the greatest of difficulty, if at all. As noted above, light serves to promote the decomposition further complicating further use and processing of the halogenated hydrocarbons.

This defect is especially marked in the case of 1,1,1-trichloroethane which is more inclined to split off hydrochloric acid and then blacken than any of the other above-named chlorinated hydrocarbons. The decomposition reaction can progress to the complete resinification of the material. Accordingly, its usefulness as such is severely limited. For industrial use, the 1,1,1-trichloroethane is employed only together with an added stabilizer.

Many agents have been suggested heretofore as stabilizers for 1,1,1-trichloroethane. These include dialkylsulfoxides, dialkylsulfites, dialkylsulfides, 1,4-dioxanes, epoxides, monoketones, trialkylsilyethers, tetralkyl compounds of tin and lead, nitroalkanes, secondary and tertiary alcohols, nitriles, acetylene alcohols, oxazirines, thiazirines, oxaphosphorines and thiaphosphorines. Usually, these stabilizing agents must be used in large quantities to provide an adequate stabilizing effect. Such is not always desirable. When large quantities are employed, the 1,1,1-trichloroethane so stabilized takes on the character of a mixture of solvents; as such its utility is limited. Additionally, use of dioxane and a number of the other conventionally employed stabilizers in such large quantities can present problems of toxicity. Certain of the conventionally used stabilizers set forth above have also proved undesirable due to the color which they impart to the 1,1,1-trichloroethane, while others are entirely unsuitable due to their great chemical reactivity with the agents to be treated where they are used up in the reaction and the stabilizing effect initially produced is gradually lost with decomposition setting in rapidly. Still another group of known stabilizers is characterized by the group's great sensitivity to hydrolysis in oxygen, and therefore, this group finds only limited application.

It has thus become desirable ti provide a stabilizer system which will stabilize 1,1,1-trichloroethane. Moreover, it is desirable to provide a stabilizer composition which will inhibit the catalytic effect of metals such as iron, aluminum and zinc. Still moreover it is desirable to provide stabilizer composition which will stabilize 1,1,1, trichloroethane in the vapor phase as well as in the liquid phase.

Still moreover it is desirable to provide a stabilized 1,1,1, trichloroethane composition which passes the test set forth in the United States military specification MIL-T-7003. This testing method is considered to be one of the strictest and thus measures the overall stability of the 1,1,1, trichloroethane particularly with respect to the amount of catalytic water present which tends to effect the decomposition. Thus, this military specification test employs a certain amount of water during the test procedure.

SUMMARY OF THE INVENTION

Broadly, this invention contemplates a stabilized 1,1,1-trichloroethane composition containing, as stabilizer therefor, a mixture consisting essentially of a nitrile, 1,4-dioxane and nitromethane.

In a particularly desirable embodiment, this invention contemplates an improved stabilized composition wherein the relative amounts of the three components stabilized composition fall within the following range:

TABLE I

| Component | Broad Range | Preferred Range |
| --- | --- | --- |
| Nitrile | 0.05 to 2.0 wt.% | 0.4 to 4.0 wt.% |
| 1,4 Dioxane | 0.4 to 5.0 wt.% | 0.5 to 3.0 wt.% |
| Nitromethane | 0.4 to 2.0 wt.% | 0.8 to 4.0 wt.% |

Generally speaking, the total amount of stabilizer present in the 1,1,1-trichloroethane composition is between 0.3 and 7 weight %, preferably, between 1.0 and 5 weight %. It is understood that, in accordance with the invention the use of only a slightly significant minor amount of methoxyacetonitrile provides a synergistic effect to a stabilizer composition containing a nitromethane and 1,4 dioxane. It will be noticed that the results are provided even when equivalent amounts of the various components of the stabilizer system are not used. Thus, in accordance with data below it is seen that synergistic results are provided when a minor amount of methoxyacetonitrile is employed. This effect is achieved in a stabilizer composition containing only 3.6 weight % stabilizer. This stabilizer is particularly effective against the catalytic decomposition effects provided by strips of iron, aluminum and zinc.

As indicated above, nitriles are broadly usable in accordance with the present invention. Those nitriles which are particularly contemplated include acetonitrile, methoxyacetonitrile, propionitrile, acrylonitrile, beta-methoxy-propionitrile, dimethylaminoacetonitrile, methylaminopropionitrile, methyleneaminocacetonitrile, dimethylaminopropionitrile, diethylaminoacetonitrile, malodinitrile, and thiodipropionitrile, as well as the mono- and poly-cyanethylated products of acetone, methylethylketone and acetic acid ester. Of the nitriles, the most preferred is methoxyacetonitrile.

It is to be understood that the present invention employs a combination of a nitrile, 1,4 dioxane and nitromethane. To the stabilizer composition of the present invention there can be added amines. The present invention prefers diamines such as ethylenediamine, in particular, as well as polyamines. Additionally, it should be mentioned that as substrate therefor there can be employed monoamines such as triallylamine, di-n-butylamine, dimethylaniline, triethylamine and n-butylamine.

When the amine is present, it is present in an amount of 0.01 weight percent and up to 0.1 weight percent, especially where the amine is ethylene diamine.

Through use of the stabilizing composition of the present invention there is provided superior stabilization of the 1,1,1-trichloroethane over stabilization provided by any of the single components used in comparable concentration. As a result of which it is possible to stabilize methylchloroform with a substantially smaller amount of stabilizer overall for general applications. The effectiveness of any of the stabilizer compositions for a specific purpose can be determined, for example, by simply boiling a specific amount of 1,1,1-trichloroethane with identical percentages of combinations to be evaluated in the presence of a specific amount of a metal powder, granules, or chips. Or alternately a strip of the metal powder can be employed. Stabilizer compositions of the present invention have been tested against compositions containing less then the ingredients of the four component system. The test has been in accordance with the United States military specification MIL-T-7003.

In table II attached hereto there is set forth data showing the relative value of stabilization of 1,1,1,-trichloroethane from several different types of stabilizers or mixtures of stabilizers. These tests have been done by utilizing the stated amount of stabilizer or stabilizer combination and 5 grams of aluminum turnings or 5 grams of aluminum granules to which was added 100 grams of 1,1,1, trichloroethane. The resulting mixture was then heated under reflux until chlorohydrocarbon blackened or until hydrogen chloride was split off. The time elapsed up to the discoloration point with evolution of HCl was taken as a measure of the effectiveness of the stated substance or combination of substances for stabilization of 1,1,1, trichloroethane. In table II there is set forth the results of no stabilizer, stabilizers wherein the sole component was an amine, a dioxane, nitromethane, an alcohol, a nitrile, a ketone or an ester. Compared against these results obtained from a two or three component system as set forth therein.

TABLE II

| | Ex. | Stabilizer | Amount Added wt.% | Time for splitting off of HCL or to blackening |
|---|---|---|---|---|
| | 1 | none | — | 1.7 min |
| -a | 2 | Triallylamine* | 0.5 | 3 min. |
| | 3 | Di-n-butylamine* | 0.5 | 6 min. |
| | 4 | Dimethylaniline* | 0.5 | 6 min. |
| | 5 | Triethylamine* | 0.5 | 7 min. |
| | 6 | n-Butylamine* | 0.5 | 8 min. |
| | 7 | Ethylene diamine* | 0.5 | 70 min. |
| -b | 8 | 1,4 Dioxane* | 0.5 | 60 min. |
| -c | 9 | Nitromethane** | 0.5 | 15 hr. |
| -d | 10 | ethyl alcohol* | 0.5 | 6 min. |
| | 11 | Allyl alcohol* | 0.5 | 9 min. |
| | 12 | Propargyl alcohol* | 0.5 | 10 min. |
| | 13 | tert. Butanol* | 0.5 | 20 min. |
| -e | 14 | Acrylonitrile* | 0.5 | 2 hr. |
| | 15 | Acetonitrile* | 0.5 | 2.5 hr. |
| | 16 | β-Methoxypropionitrile* | 0.5 | 100 min. |
| | 17 | Methyleneaminecetonitrile* | 0.5 | 1.25 hr. |
| | 18 | Dicyanethylated methylethylketone* | 0.5 | 80 min. |
| | 19 | Dicyanethylated acetic acid ester* | 0.5 | 80 min. |
| I | 20 | Acetonitrile* Ethylenediamine | 0.25 0.25 | 180 min. |
| | 21 | Acetonitrile* 1,4 dioxane | 0.25 0.25 | 173 min. |
| | 22 | β-Methoxypropionitrile (II) 1,4 dioxane | 0.25 0.25 | 36 hr. |
| | 23 | Acetonitrile* 1,4 dioxane Ethylenediamine | 0.17 0.17 0.17 | 198 min. |
| | 24 | Acetonitrile** NItromethane | 0.25 0.25 | 90 hr. |
| | 25 | Acetonitrile** tert. Butanol | 0.25 0.25 | 89 hr. |
| | 26 | Acetonitrile** Nitromethane tert. Butanol | 0.25 0.25 | 92 hr. |
| | 27 | Acetonitrile** tert. Butanol Dioxane | 0.25 0.25 0.25 | 197 hr. |

*The stabilization example was conducted in the presence of 5 grams of aluminum turnings.
**The stabilization example was conducted in the presence of 5 grams of aluminum granules.

A three-component stabilizer system of the invention containing amines was tested in a test under rigorous U.S. military specification MIL-T-7003. This testing method is considered to be one of the strictest known because in accordance with the regulations set forth therein catalytic amounts of water effecting the decomposition are also present.

There is set forth below the comparative results provided by the three component system (test E) versus a three component system consisting of ethylenediamine, or epoxibutane 1,4 dioxane and nitromethane (tests C and D). Such results demonstrate the beneficial results obtained by inclusion in such stabilizer mixture of a minor amount of nitrile, especially methoxyacetonitrile. Additionally, the data compare such a three component system with a two component system comprising 1,4 dioxane and nitromethane or a nitrile and 1,4-dioxane. From the data in Table III below it is seen that only through use of the system of the present invention is there provided a stabilized 1,1,1-trichloroethane which is clear and colorless and provides no corrosion either in the vapor phase or in the liquid phase. Note that the compositions to which they are compared all provide corrosion in the vapor phase in the presence of a zinc and aluminum strip. When present in a composition to which a strip of iron and water is present the stabilizer systems to which the one of the present invention is compared, are characterized by strong corrosion in the vapor phase as well as corrosion in the liquid phase. If a very little amount of an amine (e.g. ethylene-diamine is added to the stabilizer composition of the invention, then there is also no corrosion of iron in the vapor phase. The same results as in tests E and F are also obtained, if instead of acetomethoxinitrile there is used methoxipropiononitrile.

ethylenediamine, said ethylenediamine being present in an amount of at least 0.01 weight percent, based upon the weight of said 1,1,1-trichloroethane.

2. A stabilized 1,1,1-trichloroethane composition according to claim 1 wherein the total content of said nitrile, said 1,4-dioxane, said nitromethane and said ethylenediamine is between 0.3 and 7 weight percent,

TABLE III

| | CONTENT OF STABILIZERS (IN WT.%) | | | | | |
|---|---|---|---|---|---|---|
| | A | B | C | D | E | F |
| metoxy acetonitrile | — | 0.5 | — | — | 0,5 | 0.5 |
| 1,2-epoxy butene | — | — | — | 0,8 | — | — |
| ethylene diamine | — | — | 0.1 | — | — | 0.1 |
| 1,4-dioxane | 2.0 | 2,0 | 2.0 | 2.0 | 2,0 | 2.0 |
| nitromethane | 1.0 | — | 1.0 | 1.0 | 1,0 | 1.0 |
| reaction time (h) | 168 | 168 | 168 | 168 | 168 | 168 |
| Evaluation after completion of test: Color of the 1,1,1,-trichloroethane | strong yellow | yellow cloudy | very cloudy | strong yellow | clear yellowish (only with Fe) | clear colorless |
| Condition of the Fe-strip | --- | --- | --- | --- | — | + |
| Condition of the Fe-strip in the presence of 0.1% H$_2$O | --- | ---- | --- | --- | — | + |
| Condition of the Al-strip | — | + | — | — | + | + |
| Condition of Zn-strip | — | — | — | — | + | + |

---: strong corrosion, in the vapor phase as well as in the liquid phase
--: less strong corrosion, the vapor phase as well as in the liquid phase
—: corrosion in the vapor phase
+: no corrosion From the above it is clearly seen that the present invention's stabilizer composition effectively stabilizes 1,1,1-trichloroethane in a manner never heretofore provided. The data in the application show that the three component system of the invention with methoxyacetonitrile is superior to the single system, i.e., it is dramatically more effective under the rigorous test conditions than the two or three component systems to which it has been prepared. Hence, there is, perhaps for the first time, provided a stabilized 1,1,1-trichloroethane composition which is not adversely affected by the presence of an iron, aluminum or zinc strip even when a catalytic amount of water is present.

What is claimed is:

1. A stabilized 1,1,1-trichloroethane composition consisting essentially of 1,1,1-trichloroethane, 0.05 to 2.0 weight percent of nitrile, 0.05 to 3.0 weight percent of 1,4-dioxane, 0.1 to 2.0 weight percent nitromethane and based upon the weight of 1,1,1-trichloroethane.

3. A stabilized 1,1,1-trichloroethane composition according to claim 1 wherein the total content of said nitrile, said 1,4-dioxane, said nitromethane and said ethylenediamine is between 1.0 and 5 weight percent, based upon the weight of said 1,1,1-trichloroethane.

4. A stabilized 1,1,1-trichloroethane composition according to claim 1 wherein said ethylenediamine is present in an amount of 0.01 to 0.1 weight percent, based upon the weight of said 1,1,1,trichloroethane.

5. A stabilized 1,1,1-trichloroethane composition according to claim 1 wherein said nitrile is present in an amount of 0.1 to 1 weight percent, said 1,4-dioxane is present in amount of 0.5 to 3.0 weight percent, and said nitromethane is present in an amount of 0.2 to 1.0 weight percent.

* * * * *

UNITED STATES PATENT AND TRADEMARK OFFICE
CERTIFICATE OF CORRECTION

PATENT NO. : 4,069,265
DATED : January 17, 1978
INVENTOR(S) : Hermann Richtzenhain It is certified that error appears in the above-identified patent and that said Letters Patent are hereby corrected as shown below:

Column 2, line 16, "ti" should read -- to --.

Column 2, line 43, after "components" insert -- constituting the --.

Column 2, lines 47-50, Table 1, Preferred Range, "0.4 to 4.0" should read -- 0.1 to 1.0 --, "0.8 to 4.0" should -- 0.8 to 1.0 --, Broad Range, "0.4 to 5.0" should read -- 0.1 to 5.0 --, "0.4 to 2.0" should read -- 0.1 to 2.0 --.

Column 3, line 7, "methyleneaminocacetonitrile" should read -- methyleneaminoacetonitrile --.

Column 5, line 10, Table III "metoxy" should read -- methoxy --, B column, line 10, "--" should read -- - --.

Signed and Sealed this

Eleventh Day of July 1978

[SEAL]

Attest:

RUTH C. MASON
Attesting Officer

DONALD W. BANNER
Commissioner of Patents and Trademarks